United States Patent
Tai et al.

(10) Patent No.: US 7,678,472 B2
(45) Date of Patent: Mar. 16, 2010

(54) COMPOUND AND ORGANIC LIGHT-EMITTING DIODE AND DISPLAY UTILIZING THE SAME

(75) Inventors: Chia-Liang Tai, Hsinchu (TW); Chen-Ping Yu, Houlong Township, Miaoli County (TW); Chung-Wen Ko, Sijhih (TW)

(73) Assignee: AU Optronics Corp., Hsinchu (TW)

( * ) Notice: Subject to any disclaimer, the term of this patent is extended or adjusted under 35 U.S.C. 154(b) by 550 days.

(21) Appl. No.: 11/147,630

(22) Filed: Jun. 8, 2005

(65) Prior Publication Data

US 2006/0177691 A1 Aug. 10, 2006

(30) Foreign Application Priority Data

Feb. 5, 2005 (TW) ............... 94103960 A (51) Int. Cl.
*H01L 51/54* (2006.01)
*C07D 209/82* (2006.01)
*C07F 7/02* (2006.01)
*C09K 11/06* (2006.01)

(52) U.S. Cl. .............. 428/690; 428/917; 548/440; 556/413; 556/431; 556/432; 313/504; 313/506; 257/40; 257/E51.05

(58) Field of Classification Search .......... 428/690, 428/917; 427/58, 66; 313/502–509; 257/40, 257/88–103, E51.001–E51.052; 252/301.16–301.35; 548/440; 556/413, 431–432
See application file for complete search history.

(56) References Cited

U.S. PATENT DOCUMENTS 5,235,253 A * 8/1993 Sato .................. 315/169.3
6,310,231 B1 * 10/2001 Igarashi et al. .............. 556/489

(Continued)

FOREIGN PATENT DOCUMENTS

| CN | 1656194 | 8/2005 |
|---|---|---|
| EP | 1502936 | 2/2005 |
| JP | 07-150138 | 6/1995 |

(Continued)

OTHER PUBLICATIONS

Machine Translation of JP 2004311415.*

(Continued)

*Primary Examiner*—Dawn Garrett
(74) *Attorney, Agent, or Firm*—Thomas, Kayden, Horstemeyer & Risley

(57) ABSTRACT

An organoluminescent compound. The compound has formula (I)

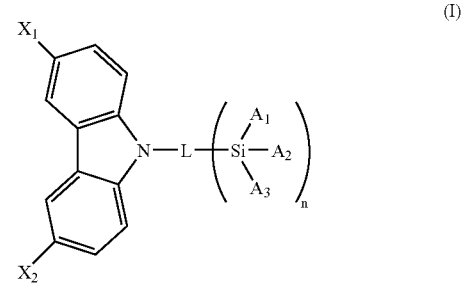

wherein $X_1$ and $X_2$ independently represent $C_{10-25}$ aryl, heteroaryl, stilbenyl, silylaryl, or arylsilyl; n represents an integer of 0 to 2; L represents aryl or heteroaryl; and $A_1$, $A_2$, and $A_3$ independently represent aryl or heteroaryl. The invention also provides an organic light-emitting diode and a display utilizing the organoluminescent compound.

13 Claims, 2 Drawing Sheets

U.S. PATENT DOCUMENTS

| | | | |
|---|---|---|---|
| 6,649,772 B2 | 11/2003 | Lin et al. | 548/439 |
| 6,660,410 B2 | 12/2003 | Hosokawa | 428/690 |
| 6,670,054 B1 * | 12/2003 | Hu et al. | 428/690 |
| 6,696,178 B2 * | 2/2004 | Igarashi | 428/690 |
| 2003/0219625 A1 * | 11/2003 | Wolk et al. | 428/690 |
| 2004/0247933 A1 * | 12/2004 | Thoms | 428/690 |
| 2005/0067951 A1 * | 3/2005 | Richter et al. | 313/504 |
| 2005/0158878 A9 | 7/2005 | Chandler | |

FOREIGN PATENT DOCUMENTS

| | | | |
|---|---|---|---|
| JP | 08-003547 | | 1/1996 |
| JP | 09-310066 | | 12/1997 |
| JP | 2002-069044 | * | 3/2002 |
| JP | 2004002351 | | 1/2004 |
| JP | 2004-071500 | | 3/2004 |
| JP | 2004-200103 | * | 7/2004 |
| JP | 2004311415 | * | 11/2004 |
| WO | WO 03/080761 A1 | | 2/2003 |
| WO | WO 03/064373 | * | 8/2003 |

OTHER PUBLICATIONS

Machine translation of JP 2004-200103. (Jul. 2004).*
Machine translation for JP 2004-071500 A published Mar. 2004.*
Derwent abstract of JP 2004-071500 A published Mar. 2004.*
CN office action mailed Feb. 29, 2008.

* cited by examiner

COMPOUND AND ORGANIC LIGHT-EMITTING DIODE AND DISPLAY UTILIZING THE SAME

BACKGROUND

The present invention relates to an compound, and more specifically to a compound used in an organic light-emitting diode.

Organic electroluminescent devices are popular in flat panel display due to their high illumination, light weight, self-illumination, low power consumption, simple fabrication, rapid response time, wide viewing angle, and no backlight requirement.

When an external electric field is applied to an organic electroluminescent device, electrons and holes are injected from cathode and anode, respectively, and then recombined to form excitons. Energy is further transported from excitons to luminescent molecules with continuous application of an electric field. Finally, luminescent molecules emit light converted from energy. A common organic electroluminescent device structure comprises an ITO anode, a hole transport layer, an emitting layer, a hole blocking layer, an electron transport layer, and a cathode. A complex organic electroluminescent device, however, may further comprise a hole injection layer disposed between an anode and a hole transport layer or an electron injection layer disposed between a cathode and an electron transport layer to improve injection efficiency of carriers, reducing driving voltage or increasing recombination thereof.

With development of synthesis techniques, various synthetic organic compounds for use in organic electroluminescent devices have been provided, with organic luminescent materials containing carbazole structure discussed herein. Currently, these luminescent materials containing carbazole structure have been used as hole transport material as disclosed in U.S. Pat. No. 6,660,410, J.P. PG-Pub. No. 2004071500, and G.P. Pat. No. 03/080761A1, as phosphorescent material as disclosed in J.P. Pat. No. 08-003547 and 09-310066, or as fluorescent material as disclosed in U.S. Pat. No. 6,649,772 and J.P. Pat. No. 07-150138.

Such related arts, however, do not disclose use of the organic luminescent materials containing carbazole structure in blue fluorescent devices. Additionally, related structures of substituted groups in 3,6-positions and nitrogen atom of carbazole are still simple, suitable for synthesis of more complicated structures. Thus, synthesis of novel blue fluorescent materials has a great potential in development of luminescent materials.

SUMMARY

The invention provides a compound having formula (I):

wherein $X_1$ and $X_2$ independently represent $C_{10-25}$ aryl, heteroaryl, stilbenyl, silylaryl, or arylsilyl; n represents an integer of 0 to 2; L represents aryl or heteroaryl; and $A_1$, $A_2$, and $A_3$ independently represent aryl or heteroaryl.

The invention also provides an organic light-emitting diode comprising a cathode, an anode, and an emitting layer, wherein the emitting layer is installed therebetween and comprises the disclosed compound having formula (I).

The invention further provides a display comprising the disclosed organic light-emitting diode and a drive circuit coupled to the organic light-emitting diode for driving the organic light-emitting diode.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION

The invention provides an organoluminescent compound having formula (I):

In formula (I), $X_1$ and $X_2$ may be the same or different substituted groups and independently represent $C_{10-25}$ aryl, heteroaryl, stilbenyl, silylaryl, or arylsilyl, such as

-continued wherein $R_1$ and $R_2$ may be the same or different substituted groups and independently represent alkyl, aryl, or heteroaryl, and Ar represents aryl. L represents aryl or heteroaryl, such as wherein each R independently represents alkyl, aryl, or heteroaryl. $A_1$, $A_2$, and $A_3$ may be the same or different substituted groups and independently represent aryl or heteroaryl, and n represents an integer of 0~2.

The specific organoluminescent compounds provided by the invention comprise -continued

The organoluminescent compound of formula (I) is prepared as follows. First, a carbazole derivative, such as 3,6-dibromo-9-phenyl carbazole, 3,6-dibromo-9-(9,9-Diethyl-9H-fluoren-2-yl)-carbazole, or 3',6'-Dibromo-9-phenyl-9H-[2,9']bicarbazole, and a boronic acid derivative, such as 1-pyrenyl boronic acid, 9,9-diphenyl-9H-fluorenyl-2-boronic acid, or 4-triphenylsilyl-phenyl boronic acid are prepared by general synthesis. Next, the carbazole derivative, boronic acid derivative, catalyst, and solvent are mixed in basic condition (such as addition of $K_2CO_3$). The catalyst may be Tetrakis(triphenylphosphine)palladium(0), Pd $(PPh_3)_4$, and the solvent may be ethanol or dimethyl ether (DME). After boiling and air-extraction, aqua-layer is extracted by solvent, such as ethyl acetate or diethyl ether. Next, organo-layer is washed with deionized water. Remaining water in the organo-layer is then removed by drying agent, such as $MgSO_4$. After the organo-layer is concentrated, precipitated mixture is purified by column to form the organoluminescent compound (formula (I)) condensed from carbazole derivative and boronic acid derivative.

Emission spectra of organoluminescent compounds containing carbazole structure provided by the invention definitely appear in blue light region due to its strongly resonated and complicated aryl groups in 3,6-positions and nitrogen atom of carbazole. Thus, such fluorescent compounds are suitable for use as hosts or dopants of emitting layer of blue fluorescent devices and provide thermal stability.

The invention also provides an organic light-emitting diode comprising a cathode, an anode, and an emitting layer, wherein the emitting layer is installed therebetween and comprises the foregoing organoluminescent compound as formula (I).

At least one of the cathode and anode is a transparent electrode. That is, the cathode and anode may be of the same or different materials, such as metal, metal alloy, or transparent metal oxide. The metal may be Al, Ca, Ag, Ni, Cr, Ti, or Mg. The metal alloy comprises Mg—Ag alloy. The transparent metal oxide comprises ITO, AZO, ZnO, InN, or $SnO_2$.

Other blue fluorescent materials may be added to the emitting layer, such as 4,4'-bis(2,2-diphenylethenyl)-1,1'-biphenyl (DPVBi), 9,10-bis[4-2,2-diphenylethenyl]phenyl]anthracene, and 9,10-di-(2-naphthyl)anthracene (ADN). The organic light-emitting diode further comprises an electron transport layer or an electron injection layer installed between the cathode and the emitting layer, or a hole transport layer or a hole injection layer installed between the anode and the emitting layer. The electron transport layer may comprise t-Bu-PBD, $Alq_3$, BeBq, TAZ, $Almq_3$, BAlq, or TPBI. The electron injection layer may comprise LiF or $Li_2O$. The hole transport layer may comprise HTM2, TPD, NPB, PPD, TBPB, spiro-TAD, spiro-NPB, TPTE2, TPTE1, NTPA, or DNPD. The hole injection layer may comprise CF—X or CF—Y. The foregoing abbreviations represent the following structures.

-continued

TPTE2

TPTE1

NTPA

-continued

DNPD t-Bu-PBD
Alq3
BeBq

TAZ
Almq3

BAlq
TPBI

Figure 1:
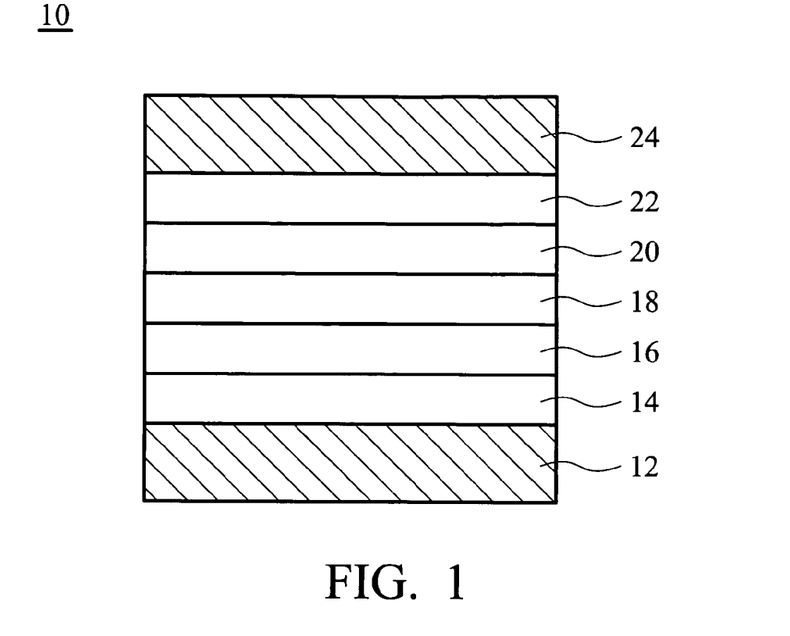
FIG. 1 is a cross section of an organic light-emitting diode of the invention.

Referring to FIG. 1, a method of fabricating an organic light-emitting diode is provided. First, an anode 12 is provided. Next, a hole injection layer 14, a hole transport layer 16, an emitting layer 18, an electron transport layer 20, an electron injection layer 22, and a cathode 24 are evaporated on the anode 12 in order. Finally, the diode is packaged to form an organic light-emitting device.

The invention also provides a display comprising the disclosed organic light-emitting diode and a drive circuit coupled to the organic light-emitting diode driving the organic light-emitting diode. The drive circuit comprises a thin film transistor.

Figure 2:
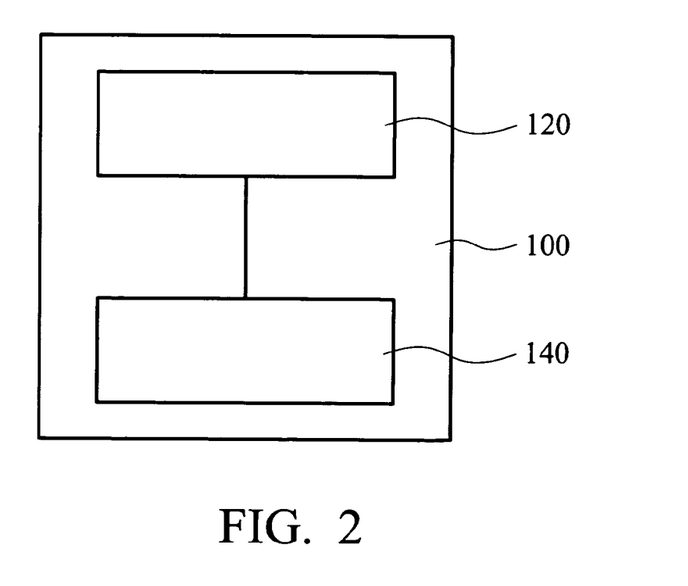
FIG. 2 is a top view of a display of the invention.

Referring to FIG. 2, a display provided by the invention is disclosed. The display 100 comprises an organic light-emitting diode 120 and a drive circuit 140 coupled to the organic light-emitting diode 120 driving the organic light-emitting diode 120.

EXAMPLES

Example 1

Preparation of Compound 6

8 g compound 1 (47.9 mmole), 7.6 ml bromobenzene (71.9 mmole), 6.8 g t-BuONa (71.9 mmole), 268 mg Pd(OAC)$_2$ (1.2 mmole), 80 ml toluene, and 970 mg t-Bu$_3$P (4.8 mmole) were added to a flask with heating and stirring, and then react overnight in the boiling state of toluene. After compound 1 was completely reacted, toluene was extracted by a rotary evaporator. Next, aqua-layer was extracted three times by adding 30 ml ethyl acetate. Next, organo-layer was washed with 60 ml deionized water. Remaining water in the organo-layer was then removed by MgSO$_4$. After the organo-layer was concentrated, precipitated dark-brown mixture was purified by a flush column (n-hexane:ethyl acetate=95:5) to form 10.4 g compound 2 and the yield thereof was 90%.

16.1 g N-Bromosuccinimide (NBS) (90.6 mmole), 10 g compound 2 (41.2 mmole), and 20 ml THF were added to a flask with ice bath and reacted at room temperature overnight. Next, 40 ml saturated sodium dithionite (Na$_2$S$_2$O$_4$) solution was added. After THF was extracted by a rotary evaporator, precipitated solids were washed with deionized water and n-hexane. Thus, 6.5 g compound 3 was prepared and the yield thereof was 70%.

8.9 ml n-BuLi (2.5 M, 22.3 mmole), 5 g compound 4 (20.3 mmole), and THF were added to a round-bottomed flask at −76° C. and stirred for 30 min. 4.6 ml trimethyl borate (40.6 mmole) (d=0.927) was then slowly dropped into the round-bottomed flask. After returning to room temperature, the solution was continuously reacted for 3 hours. Next, 20 ml deionized water and 1 ml HCl (2M) were added and stirred for 30 min. Next, organo-layer was washed with deionized water. Remaining water in the organo-layer was then removed by MgSO$_4$. After the organo-layer was concentrated, precipitated yellow solids were washed with n-hexane. Thus, 3 g compound 5 was prepared and the yield thereof was 60%.

4.9 g compound 3 (12.2 mmole), 3 g compound 5 (24.4 mmole), 1.4 g Pd(PPh$_3$)$_4$ (1.2 mmole), 5.1 g K$_2$CO$_3$ (36.6 mmole), 80 ml ethanol, and 40 ml dimethyl ether (DME) were added to a flask with heating and stirring until compound 3 was completely reacted. After solvent was extracted by a rotary evaporator, aqua-layer was extracted three times by adding 30 ml ethyl acetate. Next, organo-layer was washed with 60 ml deionized water. Remaining water in the organo-layer was then removed by MgSO$_4$. After the organo-layer was concentrated, precipitated dark-brown mixture was purified by a flush column (n-hexane:ethyl acetate=95:5) to form 4.7 g compound 6 and the yield thereof was 60%.

Example 2

Preparation of Compound 12

8 g compound 3 (47.9 mmole), 29 g 1-triphenylsiyl-4-bromobenzene (71.9 mmole), 6.8 g t-BuONa (71.9 mmole),

268 mg Pd(OAC)$_2$ (1.2 mmole), 80 ml toluene, and 970 mg t-Bu$_3$P (4.8 mmole) were added to a flask with heating and stirring. The reaction is reacted overnight in the state of boiling toluene. After compound 3 was completely reacted, toluene was extracted by a rotary evaporator. Next, aqua-layer was extracted three times by adding 30 ml ethyl acetate. Next, organo-layer was washed with 60 ml deionized water. Remaining water in the organo-layer was then removed by MgSO$_4$. After the organo-layer was concentrated, precipitated dark-brown mixture was purified by a flush column (n-hexane:ethyl acetate=95:5) to form 21.6 g compound 10 and the yield thereof was 90%.

16.1 g N-Bromosuccinimide (NBS) (90.6 mmole), 10 g compound 10 (24.2 mmole), and 20 ml THF were added to a flask with ice bath and reacted at room temperature overnight. Next, 40 ml saturated sodium dithionite (Na$_2$S$_2$O$_4$) solution was added. After THF was extracted by a rotary evaporator, precipitated solids were washed with deionized water and n-hexane. Thus, 11.1 g compound 11 was prepared and the yield thereof was 70%.

5.6 g t-BuOK (50 mole), 5 g 2-bromo-9H-fluorene (20 mmole), and THF were added to a round-bottomed flask and stirred for 30 min. 6.5 g bromoethane (60 mmole) was then added to react for 2 hours. Next, aqua-layer was extracted by adding ethyl acetate. Next, organo-layer was washed with deionized water. Remaining water in the organo-layer was then removed by MgSO$_4$. After the organo-layer was concentrated, 4.2 g yellow liquid compound 8 was prepared and the yield thereof was 70%.

6.3 ml n-BuLi (2.5 M, 15.8 mmole), 4 g compound 8 (13.2 mmole), and THF were added to a round-bottomed flask at −76° C. and stirred for 30 min. 4.4 ml trimethyl borate (39.6 mmole) (d=0.927) was then slowly dropped into the round-bottomed flask. After returning to room temperature, the mixing solution was continuously reacted for 3 hours. Next, 20 ml deionized water and 1 ml HCl (2M) were added and stirred for 30 min. Next, organo-layer was washed with deionized water. Remaining water in the organo-layer was then removed by MgSO$_4$. After the organo-layer was concentrated, precipitated yellow solids were washed with n-hexane to form 2.2 g compound 9 and the yield thereof was 73%.

5.6 g compound 11 (8.5 mmole), 2 g compound 9 (15 mmole), 1 g Pd(PPh$_3$)$_4$ (0.9 mmole), 3.2 g K$_2$CO$_3$ (23.5 mmole), 80 ml ethanol, and 40 ml dimethyl ether (DME) were added to a flask with heating and stirring until compound 11 was completely reacted. After solvent was extracted by a rotary evaporator, aqua-layer was extracted three times by adding 30 ml ethyl acetate. Next, organo-layer was washed with 60 ml deionized water. Remaining water in the organo-layer was then removed by MgSO$_4$. After the organo-layer was concentrated, precipitated dark-brown mixture was purified by a flush column (n-hexane:ethyl acetate=95:5) to form 5.6 g compound 12 and the yield thereof was 70%.

Example 3

Fabrication of Organic Light-emitting Diode

Referring to FIG. 1, a method of fabricating an organic light-emitting diode (device A) is disclosed as follows. First, an ITO anode 12 was provided on a substrate and treated with UV-O$_3$. Next, 2T-NATA was evaporated on the ITO anode 12 to form a hole injection layer 14. NPB was evaporated on the hole injection layer 14 to form a hole transport layer 16. 9-Phenyl-3,6-di-pyren-1-yl-9H-carbazole and DSA were then co-evaporated on the hole transport layer 16 to form an emitting layer 18. Next, Alq3 was evaporated on the emitting layer 18 to form an electron transport layer 20. Next, LiF was evaporated on the electron transport layer 20 to form an electron injection layer 22. Finally, Al was evaporated on the electron injection layer 22 to form a cathode 24.

Figure 3:
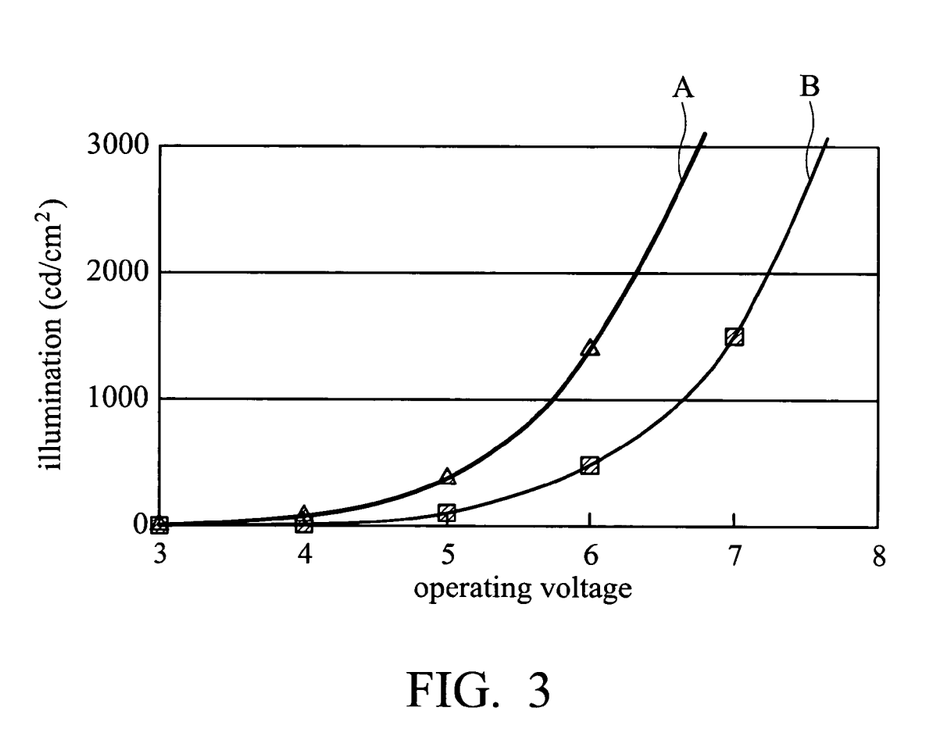
FIG. 3 shows a relationship between operating voltage and illumination of an organic light-emitting diode of the invention.

Various illuminations between device A and B were compared in FIG. 3. Structures of A and B are similar, and the distinction therebetween is merely the composition of the emitting layer. The emitting layer of device B comprises ADN and dopants. The emitting layer of device A, however, is doped with the fluorescent compound, 9-Phenyl-3,6-di-pyren-1-yl-9H-carbazole, provided by the invention.

If operating voltage is fixed at 6V, device A exhibits an illumination of 1391 cd/cm². Device B, however, merely exhibits 456 cd/cm². This shows the device provided by the invention provides higher luminant efficiency.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A compound having formula (I):

(I)

wherein $X_1$ and $X_2$ independently represent stilbenyl or silylaryl; n represents an integer of 2; L represents aryl or heteroaryl; and $A_1$, $A_2$, and $A_3$ independently represent aryl or heteroaryl.

2. The compound as claimed in claim 1, wherein $X_1$ and $X_2$ represent the same groups.

3. The compound as claimed in claim 1, wherein $X_1$ and $X_2$ are selected from wherein represents aryl.

4. The compound as claimed in claim 1, wherein L is selected from one of the following:

5. The compound as claimed in claim 1, wherein $A_1$, $A_2$, and $A_3$ represent the same groups.

6. An organic light-emitting diode, comprising:
a cathode and an anode; and
an emitting layer disposed between the cathode and anode, comprising a compound as claimed in claim 1.

7. The organic light-emitting diode as claimed in claim 6, further comprising an electron transport layer disposed between the cathode and the emitting layer.

8. The organic light-emitting diode as claimed in claim 6, further comprising an electron injection layer disposed between the cathode and the emitting layer.

9. The organic light-emitting diode as claimed in claim 6, further comprising a hole transport layer disposed between the anode and the emitting layer.

10. The organic light-emitting diode as claimed in claim 6, further comprising a hole injection layer disposed between the anode and the emitting layer.

11. The organic light-emitting diode as claimed in claim 6, wherein the compound is a blue fluorescent compound.

12. A display, comprising:
an organic light-emitting diode as claimed in claim 6; and
a drive circuit coupled to the organic light-emitting diode to drive the organic light-emitting diode.

13. The display as claimed in claim 12, wherein the drive circuit comprises a thin film transistor.

* * * * *